US010738012B2

(12) United States Patent
Samann et al.

(10) Patent No.: US 10,738,012 B2
(45) Date of Patent: Aug. 11, 2020

(54) PROCESS FOR THE PREPARATION OF AMINO-PYRAZOLES

(71) Applicant: Bayer CropScience Aktiengesellschaft, Monheim am Rhein (DE)

(72) Inventors: Christoph Samann, Duesseldorf (DE); Jason W. J. Kennedy, Cologne (DE); Sascha Von Morgenstern, Burscheid (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 16/325,573

(22) PCT Filed: Aug. 10, 2017

(86) PCT No.: PCT/EP2017/070305
§ 371 (c)(1),
(2) Date: Feb. 14, 2019

(87) PCT Pub. No.: WO2018/033467
PCT Pub. Date: Feb. 22, 2018

(65) Prior Publication Data
US 2019/0177280 A1    Jun. 13, 2019

(30) Foreign Application Priority Data

Aug. 15, 2016  (EP) .................... 16184135

(51) Int. Cl.
C07D 231/38   (2006.01)
C07C 255/66   (2006.01)
C07C 253/30   (2006.01)
C07D 231/40   (2006.01)

(52) U.S. Cl.
CPC .......... *C07D 231/38* (2013.01); *C07C 253/30* (2013.01); *C07C 255/66* (2013.01); *C07D 231/40* (2013.01)

(58) Field of Classification Search
None
See application file for complete search history.

(56) References Cited

U.S. PATENT DOCUMENTS

| 8,846,746 B2 | 9/2014 | Miura et al. |
| 9,802,899 B2 | 10/2017 | Heilmann et al. |
| 2004/0116475 A1 | 6/2004 | Shirai et al. |
| 2007/0112034 A1 | 5/2007 | Palin et al. |
| 2017/0135346 A1 | 5/2017 | Heilmann et al. |
| 2017/0305864 A1 | 10/2017 | Heilmann et al. |

FOREIGN PATENT DOCUMENTS

| WO | 2010/014453 A1 | 2/2010 |
| WO | 2011/132017 A1 | 10/2011 |
| WO | 2013/031922 A1 | 3/2013 |
| WO | 2014/053450 A1 | 4/2014 |
| WO | 2015/144652 A2 | 10/2015 |
| WO | 2015/150252 A1 | 10/2015 |
| WO | 2015/172196 A1 | 11/2015 |

OTHER PUBLICATIONS

Han, et al., "Recent development of peptide coupling reagents in organic synthesis," Tetradedron, (2004), vol. 60: 2447-2476.
Valeur, et al., "Amide bond formation: beyond the myth of coupling reagents," Chemical Society Reviews, (2009), vol. 38: 606-631.
Rao, et al., "Copper-Catalyzed sequential N-arylation of C-amino-NH-azoles," Chem.Commun. (2014), vol. 50: 12911-12914.
PCT International Search Report for PCT/EP2017/070305, dated Sep. 14, 2017.
Duffin, et al., "The Reaction of Diazonium Salts with 1-Aryl-Δ2-pyrazolines," J. Chem. Soc., (1954), 408-415.
Dorn, et al., "Uber die Cyanathylierung N-monosubstituierter Hydrazine," Chem. Ber., (1965), vol. 98: 3377-3384.
Lyngso, et al., "Solid-Phase Synthesis of 3-Amino-2-Pyrazolines," Tetrahedron Letters, (1998), vol. 39: 5845-5848.
Jagerovic, et al., "Long-Acting Fentanyl Analogues: Synthesis and Pharmacology of N-(1-Phenylpyrazolyl)-N-(1-phenylalkyl-4-piperidyl)propanamides," Bioorganic & Medicinal Chemistry, (2002), vol. 10, 817-827.
Diaz, et al., "Synthesis and Biological Evaluation of the 1-Arylpyrazole Class of σ1 Receptor Antagonists: Identification of 4-{2-[5-Methyl-1-(naphthalen-2-yl)-1H-pyrazol-3-yloxy]ethyl}morpholine (S1RA, E-52862)," J. Med. Chem., (2012), vol. 55: 8211-8224.
Bagley, et al., "Regiocontrolled synthesis of 3- and 5-aminopyrazoles, pyrazolo [3,4-d]pyrimidines, pyrazolo[3,4-b]pyridines and pyrazolo[3,4-b] quinolinones as MAPK inhibitors," Tetrahedron, (2013), vol. 69, 8429-8438.
Bagley, et al., "Microwave-Assisted Synthesis of a MK2 Inhibitor by Suzuki-Miyaura Coupling for Study in Werner Syndrome Cells," Pharmaceuticals, (2015), vol. 8: 257-276.
Stanovnik, et al., "Pyrazoles," Sci. Synth., (2002), Section 12, 15-225.
El Aazab, et al., "Design and Efficient Synthesis of Some Azole and Thiazole Systems Based 3-(1,3-Dioxoisoindolin-2-yl)-3-oxopropanenitrile," Lett. Org. Chem., (2015), vol. 12: 187-196.
Suh, et al., "Diversification of Pyrazoles by Microwave-assisted Ligand Free Copper Catalyzed N-Arylation," Bull. Korean Chem. Soc., (2012), vol. 33, No. 6: 2067-2070.
Hahn, W.E., "Cyanoethylation of Hydrazine Derivatives. I. Synthesis of a-Cyanoethylphenylhydrazine and a-Cyanoethylphenylhydrazones of Aldehydes," Societatis Scientiarum Lodziensis, Acta Chimica, (1962), vol. 8: 37-43.
Maleki, et al., "Aromatization of 1,3,5-Trisubstituted of 4,5-Dihydro-1H-Pyrazoles by In-Situ Generation of I+ from Hydrogen Peroxide/ Acids/Iodide Potassium or Sodium Systems," Bull. Korean Chem. Soc., (2011), vol. 32, No. 12: 4366-4370.

*Primary Examiner* — Kamal A Saeed
(74) *Attorney, Agent, or Firm* — McBee Moore & Vanik IP, LLC

(57) ABSTRACT

The present invention discloses an efficient preparation of 3-amino-1-((2,6-di-substituted)phenyl)pyrazoles.

10 Claims, No Drawings

US 10,738,012 B2

PROCESS FOR THE PREPARATION OF AMINO-PYRAZOLES

CROSS-REFERENCE TO RELATED APPLICATIONS

This application is a National Stage entry of International Application No. PCT/EP2017/070305, filed Aug. 10, 2017, which claims priority to European Patent Application No. 16184135.8, filed Aug. 15, 2016.

BACKGROUND

Field

The present invention discloses an efficient preparation of 3-amino-1-((2,6-di-substituted)phenyl)pyrazoles of formula (I)

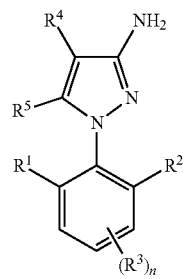

in which $R^1$, $R^2$, $R^3$, $R^4$, $R^5$, and n have the meanings mentioned below,
via a reaction sequence of Michael addition of an acrylonitrile to a phenyl hydrazine, cyclization of the corresponding Michael adduct and subsequent oxidation of the resulting 5-amino-1-phenyl-3,4-dihydropyrazole.

Compounds of formula (I) and their derivatives are important building blocks for the synthesis of bio-active compounds that can be used e.g. for the control of unwanted harmful pests.

Description of Related Art

It is known, that various amido-pyrazoles have demonstrated important applications as, for example, pest control agents (e.g. WO 2014/053450 A1, WO 2015/144652 A2, WO 2015/150252 A1).

The synthesis of 3-amino-1-phenyl-pyrazoles has been described in literature. The classical synthesis is a two-step process. At first, 5-amino-1-phenyl-3,4-dihydropyrazoles are prepared as intermediates by the reaction of a phenyl hydrazine with an acrylonitrile in ethanol with a large excess of NaOEt (*J. Chem. Soc.* 1954, 408; *Chem. Ber.* 1965, 98, 3377; *Tetrahedron Lett.* 1998, 39, 5845). The reaction reportedly occurs via a Michael addition to give an α-cyanoethylhydrazine intermediate, which then cyclizes in situ to the 5-amino-3,4-dihydropyrazole. Subsequently, these dihydropyrazole derivatives are oxidized to the corresponding 3-amino-pyrazoles most commonly by using oxidants like DDQ (US 2007/0112034 A1; *Bioorg. Med. Chem.* 2002, 10, 817), p-Chloranil (WO 2013/031922 A1), $MnO_2$ (*J. Med. Chem.* 2012, 55, 8211; US 2004/0116475 A1) or NBS (WO 2011/132017 A1).

Another possibility is the direct conversion of phenyl hydrazines to the corresponding 3-amino-1-phenyl-pyrazoles. In this case, the hydrazine is reacting with acrylonitrile derivatives bearing a leaving group on the double bond. Common examples are the reaction of phenyl hydrazines with 3-methoxyacrylonitrile (*Tetrahedron* 2013, 69, 8429; *Pharmaceuticals* 2015, 8, 257), with 3-chloro-acrylonitrile (*Sci. Synth.* 2002, 12, 15) or with 3-$Me_2$N-acrylonitrile derivatives (*Lett. Org. Chem.* 2015, 12, 187).

Another synthetic pathway is the C—N-coupling between phenyl halides and 3-aminopyrazole. There is some precedent for such couplings, and selectivity between the three nitrogens in the pyrazole unit seems to favour arylation at the desired 1-position. Several copper-catalysed couplings of 3-aminopyrazole with aryl iodides (WO 2015/172196 A1; *Bull. Korean Chem. Soc.* 2012, 33, 2067) or with phenyl boronic acids (WO 2010/014453 A1; *Chem. Comm.* 2014, 50, 12911) have been reported.

In general, the above described methods cannot be used for the synthesis of 3-amino-1-((2,6-di-substituted)phenyl) pyrazoles of formula (I). Literature examples bear either no or only a single ortho-substituent on the phenyl ring. It is noteworthy that like this only derivatives with very limited substitution patterns can be synthesized. Hence, there is still an unmet need for a general, simple, and scalable synthesis of 3-amino-1-((2,6-di-substituted)phenyl)pyrazoles.

This problem was solved by inventing a stepwise reaction sequence that starts from readily available compounds and does not rely on expensive catalysts or requires chemistry or reagents that are disadvantageous for large scale productions from a safety, economical, or environmental point of view (Scheme 1).

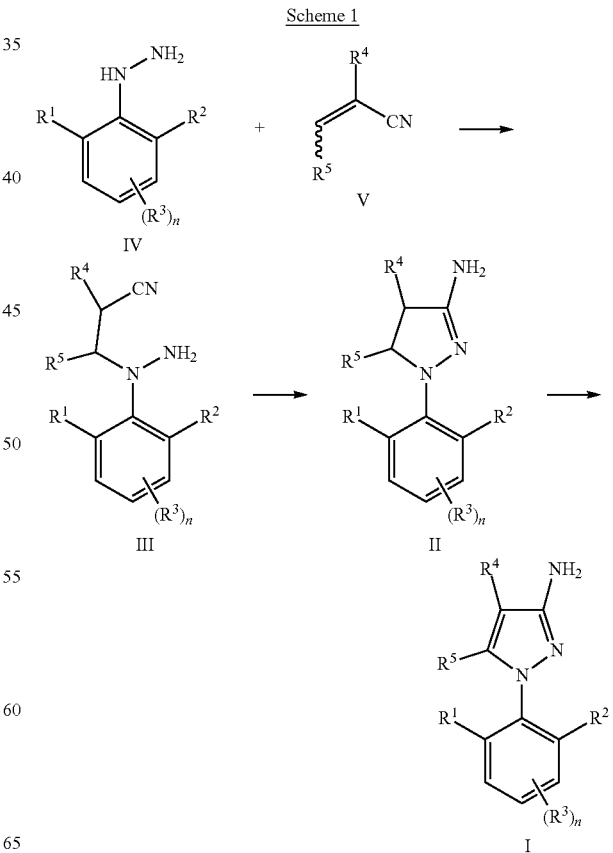

SUMMARY

The present invention describes the straightforward and convenient preparation of compounds of formula (I). It turned out that a selective preparation of the Michael adduct of formula (III) is necessary in order to synthesize the desired compounds of formula (I) in good yield and purity. Starting from hydrazines of formula (IV) and acrylonitriles of formula (V) a selective base-catalyzed Michael addition furnishes compounds of formula (III) that selectively and straightforward undergo an acid-triggered cyclization to compounds of formula (II). These compounds can subsequently be oxidized to the desired compounds of formula (I). This is in contrast to the above mentioned concerted Michael addition of hydrazines and acrylonitriles with in situ cyclization in the presence of at least stoichiometric amounts of base (*J. Chem. Soc.* 1954, 408; *Chem. Ber.* 1965, 98, 3377; *Tetrahedron Lett.* 1998, 39, 5845). This methodology does not work satisfactorily with 2,6-di-substituted phenyl hydrazines, in particular 2,6-difluoro substituted phenyl hydrazines (cf. Comparative Example 3').

The synthesis described in this invention starts with the preparation of the Michael adduct of formula (III) via the base-catalyzed addition of acrylonitriles of formula (V) to phenyl hydrazines of formula (IV) (Scheme 2).

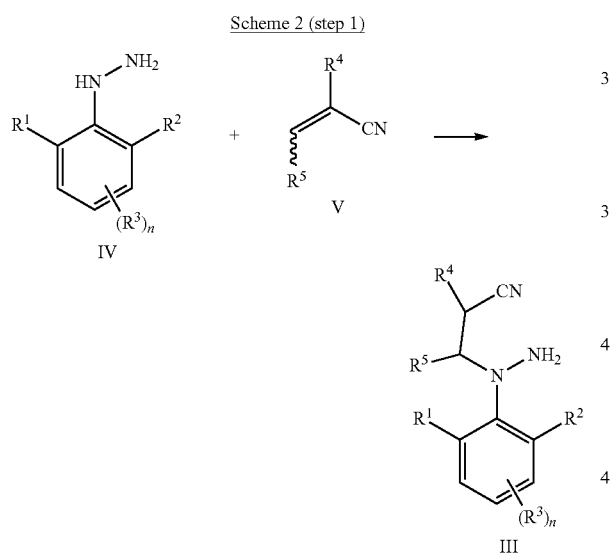

Hahn reported the selective addition of acrylonitrile to phenyl hydrazine in presence of catalytic amounts of NaOH (50%) and NEt$_3$ furnishing exclusively the α-cyanoethyl isomer (*Soc. Sci. Lodz., Acta Chim.* 1962, 8, 37). He emphasized the importance of the strict observation of the reaction conditions, e.g. the fast distillation of the Michael adduct from the reaction mixture. Otherwise cyclization to the corresponding dihydro-pyrazole was observed. Surprisingly, it was found that for 2,6-disubstituted phenyl hydrazines only catalytic amounts of only one base are required. It was also found that neither the presence of NEt$_3$ was necessary for the addition reaction nor in situ cyclization was observed when the Michael adduct has not been distilled off directly from the reaction mixture.

The next step in this invention is the acid-mediated cyclization of the Michael adduct of formula (III) to the 5-amino-1-phenyl-3,4-dihydropyrazoles of formula (II) (Scheme 3).

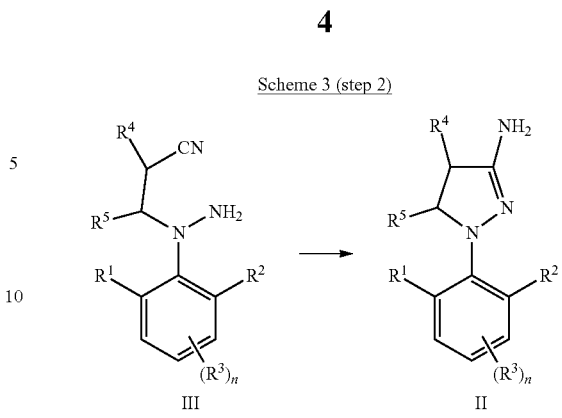

Literature known procedures like the above mentioned concerted Michael addition of hydrazines and acrylonitriles with in situ cyclization are commonly using large excess of bases, in general alkoxides in their corresponding alcohols as solvents (*J. Chem. Soc.* 1954, 408; *Chem. Ber.* 1965, 98, 3377; *Tetrahedron Lett.* 1998, 39, 5845). Surprisingly, it was found that Michael adducts of formula (III) give with acids, preferably strong acids, quick and clean reactions to the desired cyclized products of formula (II). This is even more surprising since base-catalysed cyclizations with Michael adducts of formula (III) were not nearly as efficient as the acid-catalysed reaction, giving slower reactions with the formation of side products and low to hardly any yield.

The third step in this invention is the oxidation of phenyl-dihydropyrazoles of formula (II) to the desired 2,6-di-substituted phenyl hydrazines of formula (I) (Scheme 4).

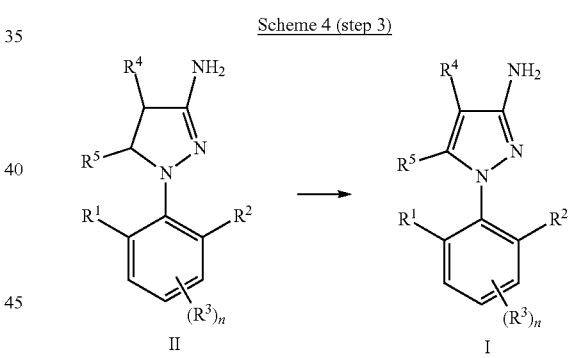

As mentioned above, literature described procedures most commonly use the following oxidants for this reaction: DDQ (US 2007/0112034 A1; *Bioorg. Med. Chem.* 2002, 10, 817), p-Chloranil (WO 2013/031922 A1), MnO$_2$ (*J. Med. Chem.* 2012, 55, 8211; US 2004/0116475 A1) or NBS (WO 2011/132017 A1). However, these reagents are disadvantageous for large scale productions from a safety, economical, or environmental point of view.

This problem was solved by inventing a simple, environmental friendly and cost-effective protocol. Maleki et al. described a one-pot procedure for the synthesis of pyrazoles via aromatization of substituted dihydropyrazoles by using a H$_2$O$_2$/AcOH/KI system (*Bull. Korean Chem. Soc.* 2011, 32, 4366). The best results reported were obtained with 10 equiv. H$_2$O$_2$, 2 equiv. AcOH and 1 equiv. KI. It was reported that reducing e.g. the amount of KI led directly to a strong decrease in yield. Also phenyl-dihydropyrazole of formula (II) can be oxidized to the desired 2,6-di-substituted phenyl hydrazines of formula (I) by using this methodology. However, very surprisingly it was found that the equivalents of the applied reagents can be dramatically decreased without any loss in yield or selectivity. Hence much less than 10 equiv. of the oxidant (preferably $H_2O_2$) and only catalytic amounts of an iodide source were necessary.

The present application is directed to each step 1 to 3 per se, to the combination of all three steps, to the combination of step 1 and step 2 and also to the combination of step 2 and step 3.

The present invention discloses an efficient synthetic pathway for the preparation of compounds of formula (I)

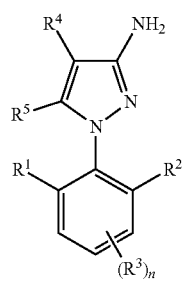

in which $R^1$, $R^2$ and $R^3$ represent independently of one another halogen, cyano, nitro, ($C_1$-$C_6$)alkyl, ($C_2$-$C_6$)alkenyl, ($C_2$-$C_6$) alkynyl, ($C_3$-$C_6$)cycloalkyl, ($C_1$-$C_6$)alkoxy, ($C_2$-$C_6$)alkenoxy, ($C_2$-$C_6$)alkynoxy, ($C_3$-$C_6$)cycloalkoxy, phenyl($C_1$-$C_6$)alkyl, aryl, cyano($C_1$-$C_6$)alkyl, halogen($C_1$-$C_6$)alkyl with 1-9 identical or different halogen atoms, halogen($C_3$-$C_6$)cycloalkyl with 1-9 identical or different halogen atoms, halogen($C_1$-$C_6$)alkoxy with 1-9 identical or different halogen atoms, ($C_1$-$C_6$)alkoxycarbonyl($C_1$-$C_6$) alkyl, ($C_1$-$C_6$)alkoxy($C_1$-$C_6$)alkyl, ($C_1$-$C_6$)alkylthio, halogen($C_1$-$C_6$)alkylthio with 1-9 identical or different halogen atoms, ($C_1$-$C_6$)alkylsulfinyl, halogen($C_1$-$C_6$) alkylsulfinyl with 1-9 identical or different halogen atoms, ($C_1$-$C_6$)alkylsulfonyl, halogen($C_1$-$C_6$)alkylsulfonyl with 1-9 identical or different halogen atoms, n represents a number from the group consisting of 0, 1 and 2, where for n>1 $R^3$ may be identical or different and $R^4$ and $R^5$ represent independently of one another hydrogen, cyano, nitro, ($C_1$-$C_6$)alkyl, ($C_3$-$C_6$)cycloalkyl, ($C_1$-$C_6$) alkoxy, ($C_3$-$C_6$)cycloalkoxy, phenyl($C_1$-$C_6$)alkyl, aryl, heteroaryl, cyano($C_1$-$C_6$)alkyl, halogen($C_1$-$C_6$)alkyl with 1-9 identical or different halogen atoms, halogen($C_1$-$C_6$) alkoxy with 1-9 identical or different halogen atoms, ($C_1$-$C_6$)alkoxycarbonyl($C_1$-$C_6$)alkyl, ($C_1$-$C_6$)alkoxy($C_1$-$C_6$)alkyl, ($C_1$-$C_6$)alkylthio, halogen($C_1$-$C_6$)alkylthio with 1-9 identical or different halogen atoms, ($C_1$-$C_6$)alkylsulfinyl, halogen($C_1$-$C_6$)alkylsulfinyl with 1-9 identical or different halogen atoms, ($C_1$-$C_6$)alkylsulfonyl, halogen ($C_1$-$C_6$)alkylsulfonyl with 1-9 identical or different halogen atoms.

When $R^1$, $R^2$, $R^3$, $R^4$ or $R^5$ represent aryl, it is a phenyl, naphthyl, or anthracenyl group, and is unsubstituted or is substituted with 1-4 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), halogens, nitro groups, nitrile groups, or groups of the structure C(=O)NR$^a$R$^b$ (where R$^a$ and R$^b$ are independently chosen between H and a $C_{1-4}$-alkyl group (which may be straight-chained or branched)).

When $R^4$ or $R^5$ represent heteroaryl, it is a 4-, 5-, or 6-membered ring containing 1-4 heteroatoms independently chosen between O, N, and S, and is in particular selected from the group consisting of

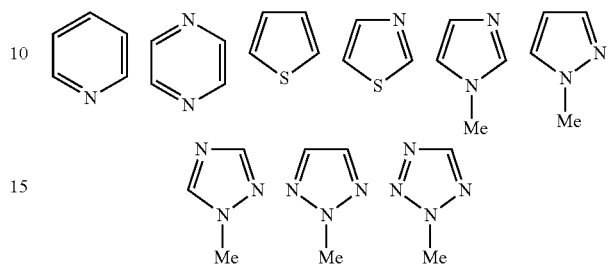

which may be connected to the rest of the molecule through any of the ring carbon atoms. This heterocycle is unsubstituted or is substituted with 1-3 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained or branched), nitriles, nitro groups, halogens, or groups of the structure C(=O)NR$^a$R$^b$ (where R$^a$ and R$^b$ are independently chosen between H or a $C_{1-4}$-alkyl group (which may be straight-chained or branched)).

DETAILED DESCRIPTION OF A PREFERRED EMBODIMENT

In a preferred embodiment of the invention $R^1$, $R^2$ and $R^3$ represent independently of one another halogen, cyano, nitro, ($C_1$-$C_3$)alkyl, ($C_2$-$C_3$)alkenyl, ($C_2$-$C_3$) alkynyl, ($C_3$-$C_6$)cycloalkyl, ($C_1$-$C_3$)alkoxy, phenyl($C_1$-$C_3$)alkyl, aryl, cyano($C_1$-$C_3$)alkyl, halogen($C_1$-$C_3$)alkyl with 1-7 identical or different halogen atoms, halogen($C_1$-$C_3$)alkoxy with 1-7 identical or different halogen atoms, ($C_1$-$C_3$)alkoxycarbonyl($C_1$-$C_3$)alkyl, ($C_1$-$C_3$)alkoxy($C_1$-$C_3$)alkyl, ($C_1$-$C_3$)alkylthio, halogen($C_1$-$C_3$)alkylthio with 1-7 identical or different halogen atoms, ($C_1$-$C_3$)alkylsulfinyl, ($C_1$-$C_3$)alkylsulfonyl, n represents a number from the group consisting of 0, 1 and 2, where for n>1 $R^3$ may be identical or different and $R^4$ and $R^5$ represent independently of one another hydrogen, cyano, ($C_1$-$C_3$)alkyl, ($C_3$-$C_6$)cycloalkyl, ($C_1$-$C_3$)alkoxy, phenyl($C_1$-$C_3$)alkyl, aryl, heteroaryl, cyano($C_1$-$C_3$)alkyl, halogen($C_1$-$C_3$)alkyl with 1-7 identical or different halogen atoms, halogen($C_1$-$C_3$)alkoxy with 1-7 identical or different halogen atoms, ($C_1$-$C_3$)alkoxycarbonyl($C_1$-$C_3$) alkyl, ($C_1$-$C_3$)alkoxy($C_1$-$C_3$)alkyl, ($C_1$-$C_3$)alkylthio, halogen($C_1$-$C_3$)alkylthio with 1-9 identical or different halogen atoms.

When $R^1$, $R^2$, $R^3$, $R^4$ or $R^5$ represent aryl, it is a phenyl or naphthyl group, and is unsubstituted or is substituted with 1-3 substituents independently chosen from the following list: $C_{1-3}$-alkyl groups (which may be straight-chained, cyclic, or branched), $C_{1-3}$-haloalkyl groups (which may be straight-chained, cyclic, or branched), $C_{1-3}$-alkoxy groups (which may be straight-chained, cyclic, or branched), halogens, nitro groups, nitrile groups, or groups of the structure C(=O)NR$^a$R$^b$ (where R$^a$ and R$^b$ are independently chosen between H and a $C_{1-3}$-alkyl group (which may be straight-chained or branched)).

When R⁴ or R⁵ represent heteroaryl, it is a 4-, 5-, or 6-membered ring containing 1-4 heteroatoms independently chosen between O, N, and S, and is in particular selected from the group consisting of

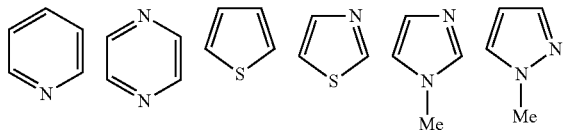

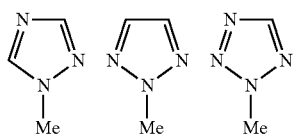

which may be connected to the rest of the molecule through any of the ring carbon atoms. This heterocycle is unsubstituted or is substituted with 1-3 substituents independently chosen from the following list: $C_{1-3}$-alkyl groups (which may be straight-chained, cyclic, or branched), $C_{1-3}$-haloalkyl groups (which may be straight-chained, cyclic, or branched), $C_{1-3}$-alkoxy groups (which may be straight-chained or branched), nitriles, nitro groups, halogens, or groups of the structure $C(=O)NR^aR^b$ (where $R^a$ and $R^b$ are independently chosen between H or a $C_{1-3}$-alkyl group (which may be straight-chained or branched)).

In a particular preferred embodiment of the invention

R¹, R² and R³ represent independently of one another bromo, chloro, fluoro, cyano, $(C_1$-$C_3)$alkyl, $(C_1$-$C_3)$alkoxy, trifluoromethyl, trifluoromethoxy, $(C_1$-$C_3)$alkylthio, n represents a number from the group consisting of 0 and 1, where for n=1 R³ is preferred in position 4 and R⁴ and R⁵ represent independently of one another hydrogen, cyano, $(C_1$-$C_3)$alkyl, $(C_1$-$C_3)$alkoxy, trifluoromethyl, $(C_1$-$C_3)$alkylthio.

In a very particular preferred embodiment of the invention

R¹, R² and R³ represent independently of one another chloro, fluoro, trifluoromethyl, n represents a number from the group consisting of 0 and 1, where for n=1 R³ is in position 4 and R⁴ and R⁵ represent hydrogen.

In another very particular preferred embodiment of the invention

R¹ represents fluoro,

R² represents fluoro, n represents 0,

R⁴ represents hydrogen and

R⁵ represents hydrogen.

3-Amino-1-((2,6-di-substituted)phenyl)pyrazoles of formula (I) are prepared from 5-amino-1-((2,6-di-substituted) phenyl)dihydropyrazoles of formula (II)

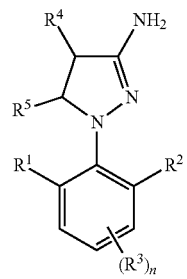

in which R¹, R², R³, R⁴, R⁵ and n have the same definitions as provided above for the compounds of formula (I) via oxidation with an oxidative system consisting of an oxidant, an iodide source and an acid.

The oxidation of dihydropyrazoles of formula (II) to pyrazoles of formula (I) may be performed neat or in the presence of a solvent. In reactions where a solvent is used, solvents such as amides (e.g. DMF, DMAc, NMP), nitriles (e.g. MeCN, PrCN), alcohols (e.g. MeOH, EtOH, (i)-PrOH, (n)-BuOH), ethers (e.g. Et₂O, 2-methyltetrahydrofuran, THF, MTBE), esters (e.g. MeOAc, EtOAc, (i)-PrAc, BuOAc), carbonates (e.g. dimethyl carbonate, diethyl carbonate, ethylene carbonate, propylene carbonate), aromatic hydrocarbons or halogenated derivatives thereof (e.g. toluene, xylene, chlorobenzene), hydrocarbons or halogenated derivatives thereof (e.g. methylcyclohexane, heptane, dichloromethane, dichloroethane), sulfoxides (e.g. dimethylsulfoxide, sulfolane), ketones (e.g. acetone, methylisobutylketone), or water may be used either singly or as a mixture of two or more thereof. The use of nitriles, alcohols, water, or mixtures thereof is preferred. Especially preferred is the use of MeOH, EtOH, (i)-PrOH, (n)-BuOH, MeCN, PrCN, water, or mixtures of two or more of these solvents.

When the oxidation is performed in a solvent or a mixture of solvents, the concentration of the dihydropyrazoles of formula (II) in the resulting mixture may lie between 1%-50% (w/w), although a range from 10%-40% (w/w) is preferred.

The oxidant may be an inorganic peroxide, such as H₂O₂ or an organic peroxide like alkyl hydroperoxides or alkylaryl hydroperoxides. Preferred oxidant is H₂O₂. In general 1 equiv. of the dihydropyrazoles of formula (II) is reacted with 0.9 equiv. to 5 equiv. of the oxidant, preferably with 1-3 equiv. and more preferably with 1-2 equiv. of the oxidant.

The iodide source may be an inorganic iodide salt, such as NaI, KI, CsI or AgI or another iodide containing compound like HI. Preferred iodide source is NaI, KI or HI. The reaction stoichiometry between the dihydropyrazoles of formula (II) and the iodide source may range from 0.01 equiv. to 0.5 equiv., although a range from 0.02-0.5 equiv. is preferred and a range from 0.02-0.1 equiv. is particularly preferred.

The acid may be a mineralic acid (e.g. HI), carboxylic acid (e.g. formic acid, acetic acid) or a sulfonic acid (e.g. MsOH, pTsOH). Preferred acid is a carboxylic acid or HI. In general 1 equiv. of the dihydropyrazoles of formula (II) is reacted with 0.1 equiv. to 1 equiv. of the acid, preferably with 0.2-1 equiv. and more preferably with 0.2-0.8 equiv. of the acid.

The reaction may be carried out between −40° C. and 180° C., and is preferably carried out between −10° C. and 120° C. and particular preferably between 10° C. and 90° C.

The reaction may be carried out between 0.1 bar and 10 bar pressure, and is preferably carried out between 0.8 bar and 1.2 bar.

5-Amino-1-((2,6-di-substituted)phenyl)dihydropyrazoles of formula (II) are prepared from α-cyanoethyl hydrazines of formula (III)

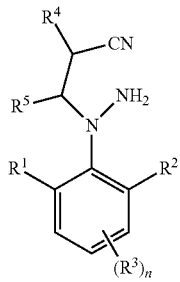

in which $R^1$, $R^2$, $R^3$, $R^4$, $R^5$ and n have the same definitions as provided above for the compounds of formula (II) via acid-mediated cyclization.

The cyclization of α-cyanoethyl hydrazines of formula (III) to dihydropyrazoles of formula (II) may be performed neat or in the presence of a solvent. In reactions where a solvent is used, solvents such as amides (e.g. DMF, DMAc, NMP), nitriles (e.g. MeCN, PrCN), alcohols (e.g. MeOH, EtOH, (i)-PrOH, (n)-BuOH), ethers (e.g. $Et_2O$, 2-methyltetrahydrofuran, THF, MTBE), esters (e.g. MeOAc, EtOAc, (i)-PrAc, BuOAc), carbonates (e.g. dimethyl carbonate, diethyl carbonate, ethylene carbonate, propylene carbonate), aromatic hydrocarbons or halogenated derivatives thereof (e.g. toluene, xylene, chlorobenzene), hydrocarbons or halogenated derivatives thereof (e.g. methylcyclohexane, heptane, dichloromethane, dichloroethane), sulfoxides (e.g. dimethylsulfoxide, sulfolane), ketones (e.g. acetone, methylisobutylketone), or water may be used either singly or as a mixture of two or more thereof. The use of no solvent or the use of nitriles, alcohols, ethers, esters, water, or mixtures thereof is preferred. Especially preferred is the use of nitriles, ethers, esters or water, or mixtures of two or more of these solvents.

When the cyclization is performed in a solvent or a mixture of solvents, the concentration of the dihydropyrazoles of formula (II) in the resulting mixture may lie between 1%-50% (w/w), although a range from 10%-40% (w/w) is preferred.

The acid may be a mineral acid (e.g., HCl, $H_2SO_4$, $H_3PO_4$) or an organic acid (e.g., $CF_3CO_2H$, $CH_3SO_3H$, $CF_3SO_3H$, pTsOH, MsOH). Preferred acid is a mineral acid like HCl or $H_2SO_4$. In general 1 equiv. of the α-cyanoethyl hydrazine of formula (III) is reacted with 0.01 equiv. to 10 equiv. of the acid, preferably with 0.1-5 equiv. and more preferably with 0.1-2 equiv. of the acid.

The reaction may be carried out between −40° C. and 180° C., and is preferably carried out between −10° C. and 150° C. and particular preferably between 40° C. and 120° C.

The reaction may be carried out between 0.1 bar and 10 bar pressure, and is preferably carried out between 0.8 bar and 1.2 bar.

α-Cyanoethyl hydrazines of formula (III) are prepared from (2,6-di-substituted)phenyl hydrazines of formula (IV) and acrylonitriles of formula (V)

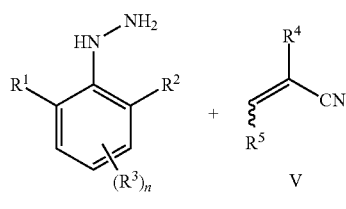

in which $R^1$, $R^2$, $R^3$, $R^4$, $R^5$ and n have the same definitions as provided above for the compounds of formula (III) via base-catalyzed Michael addition.

The reaction may be performed using a free hydrazine of formula (IV) or using a salt of such a hydrazine. When such a salt is used, it may be a hydrochloride, hydrobromide, sulfate, acetate, trifluoroacetate, methanesulfonate, or 4-toluenesulfonate salt of a hydrazine of formula (IV). Preferred is the use of a free hydrazine or a hydrochloride salt thereof. Many of these hydrazines of formula (IV) are commercially available or easy to synthesize, e.g. via diazotization of the corresponding phenyl halide and subsequent reduction.

One skilled in the art will further be aware that acrylonitriles of formula (V) can exist as E- or Z-isomers, and that these isomers can interconvert. If desired, these isomers can generally be separated by standard isolation techniques (e.g., chromatography, recrystallization, distillation). The present invention includes the use of either of these isomeric forms and mixtures thereof. Many of these acrylonitriles of formula (V) are commercially available.

The Michael addition of (2,6-di-substituted)phenyl hydrazines of formula (IV) and acrylonitriles of formula (V) may be performed neat or in the presence of a solvent. In reactions where a solvent is used, solvents such as amides (e.g. DMF, DMAc, NMP), nitriles (e.g. MeCN, PrCN), alcohols (e.g. MeOH, EtOH, (i)-PrOH, (n)-BuOH), ethers (e.g. $Et_2O$, 2-methyltetrahydrofuran, THF, MTBE), esters (e.g. MeOAc, EtOAc, (i)-PrAc, BuOAc), carbonates (e.g. dimethyl carbonate, diethyl carbonate, ethylene carbonate, propylene carbonate), aromatic hydrocarbons or halogenated derivatives thereof (e.g. toluene, xylene, chlorobenzene), hydrocarbons or halogenated derivatives thereof (e.g. methylcyclohexane, heptane, dichloromethane, dichloroethane), sulfoxides (e.g. dimethylsulfoxide, sulfolane) or ketones (e.g. acetone, methylisobutylketone) may be used either singly or as a mixture of two or more thereof. The use of no solvent or of nitriles as solvents is preferred.

When the Michael addition is performed in a solvent or a mixture of solvents, the concentration of the dihydropyrazoles of formula (II) in the resulting mixture may lie between 1%-50% (w/w), although a range from 10%-40% (w/w) is preferred.

The base may be an inorganic base (e.g., NaOH, KOH) as water containing solution or neat or an organic base (e.g., $Et_3N$, DIPEA, alkoxides). Preferred base is an inorganic base like NaOH or KOH. In general 1 equiv. of the phenyl hydrazine of formula (IV) is reacted with about 1 equiv. of the acrylonitrile of formula (V) in the presence of 0.01 equiv. to 0.8 equiv. of the base, preferably in the presence of 0.01-0.5 equiv. and more preferably in the presence of 0.01-0.2 equiv. of the base.

The reaction may be carried out between −40° C. and 180° C., and is preferably carried out between −10° C. and 120° C. and particular preferably between 10° C. and 100° C.

The reaction may be carried out between 0.1 bar and 10 bar pressure, and is preferably carried out between 0.8 bar and 1.2 bar.

The present invention is also directed to a process for the preparation of the compound of formula (VII)

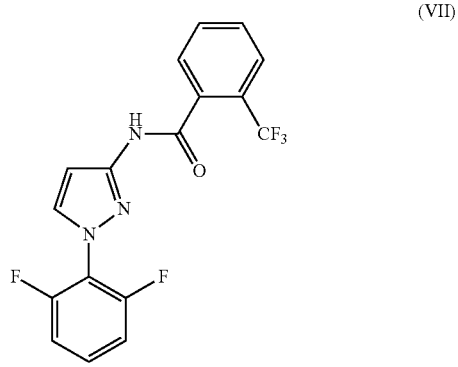 [SMILES: O=C(Nc1ccn(-c2c(F)cccc2F)n1)c1ccccc1C(F)(F)F]

(VII)

which can be obtained by reacting the compound of formula (Ia)

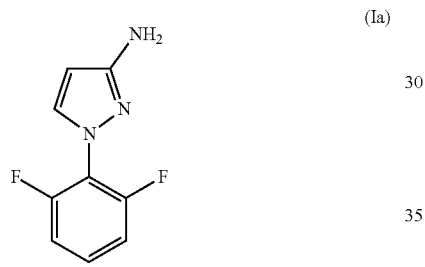

(Ia)

obtained by a process according to the present invention, with a compound of formula (VI)

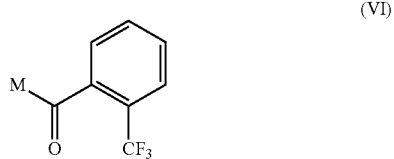

(VI)

in which
M represents halogen, hydroxy, alkoxy, alkylsulphanyl, acyloxy, N-heterocyclyl (e.g. imidazolyl) or represents hydroxyl and preferably represents halogen, more preferably chlorine.

Compounds of formula (VI) can be preactivated or be activated in situ. Compounds of formula (VI) can be employed, for example, as acid halides (e.g. M=chlorine). In this case, the reaction is advantageously carried out at elevated temperatures without base or at lower temperatures in the presence of a base such as, for example, triethylamine or sodium hydroxide. However, it is also possible to use carboxylic acids (M=OH) in the presence of coupling reagents such as, for example dicyclohexylcarbodiimide and additives such as 1-hydroxy-1-H-benzotriazole (W. König, R. Geiger, Chem. Ber. 1970, 103, 788). Use may furthermore be made of coupling reagents such as 1-ethyl-3-(3-dimethylaminopropyl)carbodiimide, 1,1'-carbonyl-1H-imidazole, O-(benzotriazol-1-yl)-N,N,N',N'-tetramethyluronium hexafluorophosphate and similar compounds. Suitable coupling reagents for carrying out the preparation process are, in principle, all compounds which allow an amide bond to be formed (cf., for example, E. Valeur, M. Bradley *Chem. Soc. Rev.* 2009, 38, 606; S.-Y. Han, Y.-A. Kim *Tetrahedron* 2004, 60, 2447). Use may furthermore also be made of symmetric or mixed anhydrides for preparing the compound of formula (VII) (G. W. Anderson, J. E. Zimmerman, F. M. Calahan, *J. Am. Chem. Soc.* 1967, 89, 5012). Here, various chloroformic esters may be employed, for example isobutyl chloroformate and sec-butyl chloroformate. Isovaleryl chloride and pivaloyl chloride, for example, may likewise be used (cf. WO 2014/53450 A1).

The compound of formula (VII) is known to be useful for controlling animal pests including arthropods, insects and nematodes, cf. WO 2014/053450 A1.

EXAMPLES

Example 1: Synthesis of 3-(N-amino-2,6-difluoro-anilino)propanenitrile

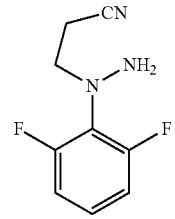 [SMILES: N#CCCN(N)c1c(F)cccc1F]

A solution of (2,6-difluorophenyl)hydrazine (88.6 g, 0.62 mol) in 250 mL MeCN was treated with 2.6 mL (0.05 mol) NaOH (50%) and heated to 50° C. Subsequently, acrylonitrile (34.3 g, 0.65 mol) was added dropwise over a period of 20 min. The temperature was kept below 60° C. After stirring for 1 h at 50° C., most of the MeCN was distilled off. The reaction was diluted with 200 mL of water extracted three times with 150 mL EtOAc. The combined organic phases were washed once with brine, dried over $Na_2SO_4$ and the solvent was evaporated to give 3-(N-amino-2,6-difluoro-anilino)propanenitrile (110.0 g, 90% yield, 96.2% HPLC-purity) as white solid.

$^1$H NMR ($CD_3CN$) δ (ppm)=7.1-7.2 (m, 1H), 6.9-7.0 (m, 2H), 4.1 (br s, 2H), 3.4 (t, 2H), 2.7 (t, 2H).

Example 2: Synthesis of 2-(2,6-difluorophenyl)-3,4-dihydropyrazol-5-amine

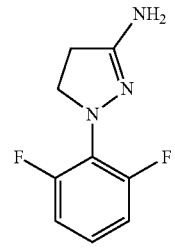 [SMILES: NC1=NN(c2c(F)cccc2F)CC1]

A solution of 3-(N-amino-2,6-difluoro-anilino)propanenitrile (110.0 g, 0.56 mol) in 200 mL MeCN was treated with 94 mL aq. HCl (32%) and heated to reflux for 5 h. The reaction mixture was cooled to 50° C. and 192 mL aq. NaOH (20%) were added. After stirring for 15 min at 50° C., the phases were separated and the organic phase was dried over Na$_2$SO$_4$. The solvent of the organic phase was removed under vacuum and the remaining solid was recrystallized from toluene to give 2-(2,6-difluorophenyl)-3,4-dihydropyrazol-5-amine (104.9 g, 95% yield, 96.8% HPLC-purity) as a light beige solid.

$^1$H NMR (CD$_3$CN) δ (ppm)=7.0-7.1 (m, 1H), 6.8-6.9 (m, 2H), 4.4 (br s, 2H), 3.6 (t, 2H), 2.8 (t, 2H).

Example 3: Synthesis of 2-(2,6-difluorophenyl)-3,4-dihydropyrazol-5-amine via 3-(N-amino-2,6-difluoro-anilino)propanenitrile as One-Pot Procedure

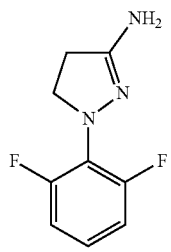

A solution of (2,6-difluorophenyl)hydrazine (35.4 g, 0.25 mol) in 100 mL MeCN was treated with 1.0 mL (0.02 mol) NaOH (50%) and heated to 50° C. Subsequently, acrylonitrile (13.7 g, 0.26 mol) was added dropwise over a period of 20 min. The temperature was kept below 60° C. After stirring for 1 h at 50° C., 38 mL aq. HCl (32%) were added and the reaction was heated to reflux for 5 h. The reaction mixture was cooled to 50° C. and 77 mL aq. NaOH (20%) were added. After stirring for 15 min at 50° C., the phases were separated and the organic phase was dried over Na$_2$SO$_4$. The solvent of the organic phase was removed under vacuum and the remaining solid was recrystallized from toluene to give 2-(2,6-difluorophenyl)-3,4-dihydropyrazol-5-amine (41.9 g, 85% yield, 96.5% HPLC-purity) as a light beige solid.

$^1$H NMR (CD$_3$CN) δ (ppm)=7.0-7.1 (m, 1H), 6.8-6.9 (m, 2H), 4.4 (br s, 2H), 3.6 (t, 2H), 2.8 (t, 2H).

Comparative Example 3': Synthesis of 2-(2,6-difluorophenyl)-3,4-dihydropyrazol-5-amine

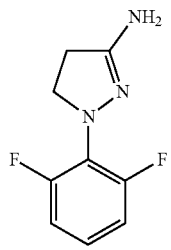 [SMILES: NC1=NN(c2c(F)cccc2F)CC1]

A solution of acrylonitrile (345 mg, 6.4 mmol) in 5 mL EtOH was treated with NaOMe (1.94 g, 10.7 mmol) at room temperature and stirred for 30 min. Then, (2,6-difluorophenyl)hydrazine (1.0 g, 5.4 mmol) was added and the reaction mixture heated to reflux overnight. The reaction mixture was cooled to room temperature and 20 mL water were added. After extraction with DCM (3×20 mL) the combined organic phases were dried over Na$_2$SO$_4$ and evaporated. 2-(2,6-difluorophenyl)-3,4-dihydropyrazol-5-amine (770 mg, 32% yield, 44.3% HPLC-purity) was obtained as brown oil.

$^1$H NMR (CD$_3$CN) δ (ppm)=7.0-7.1 (m, 1H), 6.8-6.9 (m, 2H), 4.4 (br s, 2H), 3.6 (t, 2H), 2.8 (t, 2H).

Example 4: Synthesis of 1-(2,6-difluorophenyl)pyrazol-3-amine (Ia)

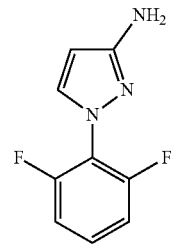 [SMILES: Nc1ccn(-c2c(F)cccc2F)n1]

To a solution of 2-(2,6-difluorophenyl)-3,4-dihydropyrazol-5-amine (10.0 g, 50.7 mmol), KI (420 mg, 2.5 mmol) and AcOH (1.5 g, 25.0 mmol) in 50 mL MeCN was added H$_2$O$_2$ (3.5 g, 53.2 mmol, 50%) at 40° C. over a period of 1 h. The temperature was kept below 65° C. After stirring for 1 h at 50° C., the reaction was quenched with 9 mL aq. NaOH (20%) and 4 mL aq. NaHSO$_3$ (40%). Then most of the MeCN was distilled off and a suspension was formed. Filtration and subsequent recrystallization of the solid gave 1-(2,6-difluorophenyl)pyrazol-3-amine (7.8 g, 80% yield, 96.7% HPLC-purity) as a beige solid.

$^1$H NMR (CD$_3$CN) δ (ppm)=7.5 (d, 1H), 7.4-7.5 (m, 1H), 7.1-7.2 (m, 2H), 5.8 (d, 1H), 4.1 (br s, 2H).

Example 5: Synthesis of N-[1-(2,6-difluorophenyl)pyrazol-3-yl]-2-(trifluoromethyl)benzamide (VII)

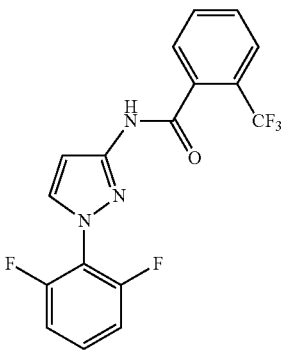 [SMILES: O=C(Nc1ccn(-c2c(F)cccc2F)n1)c1ccccc1C(F)(F)F]

To a solution of 1-(2,6-difluorophenyl)pyrazol-3-amine (56.0 g, 0.29 mmol) in 425 mL toluene 2-(trifluoromethyl)benzoyl chloride (60.4 g, 0.29 mmol) was added at 50° C. over a period of 2 h and stirred for another 1 h at 50° C. After subsequent heating to reflux for 6 h the reaction mixture was cooled down, the precipitating solid was filtered and washed twice with 100 mL toluene. N-[1-(2,6-difluorophenyl)pyrazol-3-yl]-2-(trifluoromethyl)benzamide (96.8 g, 91% yield, 99.7% HPLC-purity) was obtained as brown solid.

$^1$H NMR (CD$_3$CN) δ (ppm)=9.2 (br. s, 1H), 7.8 (d, 1H), 7.6-7.7 (m, 4H), 7.4-7.5 (m, 1H), 7.2 (t, 2H), 7.0 (d, 1H).

The invention claimed is:

1. Process for preparation of a compound of formula (I)

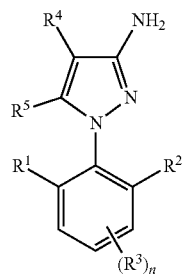

I wherein

R$^1$, R$^2$ and R$^3$ represent independently of one another halogen, cyano, nitro, (C$_1$-C$_6$)alkyl, (C$_2$-C$_6$)alkenyl, (C$_2$-C$_6$)alkynyl, (C$_3$-C$_6$)cycloalkyl, (C$_1$-C$_6$)alkoxy, (C$_2$-C$_6$)alkenoxy, (C$_2$-C$_6$)alkynoxy, (C$_3$-C$_6$)cycloalkoxy, phenyl(C$_1$-C$_6$)alkyl, aryl, cyano(C$_1$-C$_6$)alkyl, halogen(C$_1$-C$_6$)alkyl with 1-9 identical or different halogen atoms, halogen(C$_3$-C$_6$)cycloalkyl with 1-9 identical or different halogen atoms, halogen(C$_1$-C$_6$)alkoxy with 1-9 identical or different halogen atoms, (C$_1$-C$_6$)alkoxycarbonyl(C$_1$-C$_6$)alkyl, (C$_1$-C$_6$)alkoxy(C$_1$-C$_6$)alkyl, (C$_1$-C$_6$)alkylthio, halogen(C$_1$-C$_6$)alkylthio with 1-9 identical or different halogen atoms, (C$_1$-C$_6$)alkylsulfinyl, halogen(C$_1$-C$_6$)alkylsulfinyl with 1-9 identical or different halogen atoms, (C$_1$-C$_6$)alkylsulfonyl, halogen(C$_1$-C$_6$)alkcylsulfonyl with 1-9 identical or different halogen atoms, n represents a number from the group consisting of 0, 1 and 2, where for n >1 R$^3$ may be identical or different and R$^4$ and R$^5$ represent independently of one another hydrogen, cyano, nitro, (C$_1$-C$_6$)alkyl, (C$_3$-C$_6$)cycloalkyl, (C$_1$-C$_6$)alkoxy, (C$_3$-C$_6$)cycloalkoxy, phenyl(C$_1$-C$_6$)alkyl, aryl, heteroaryl, cyano(C$_1$-C$_6$)alkyl, halogen(C$_1$-C$_6$)alkyl with 1-9 identical or different halogen atoms, halogen(C$_1$-C$_6$)alkoxy with 1-9 identical or different halogen atoms, (C$_1$-C$_6$)alkoxycarbonyl(C$_1$-C$_6$)alkyl, (C$_1$-C$_6$)alkoxy(C$_1$-C$_6$)alkyl, (C$_1$-C$_6$)alkylthio, halogen(C$_1$-C$_6$)alkylthio with 1-9 identical or different halogen atoms, (C$_1$-C$_6$)alkylsulfinyl, halogen(C$_1$-C$_6$)alkylsulfinyl with 1-9 identical or different halogen atoms, (C$_1$-C$_6$)alkylsulfonyl, halogen(C$_1$-C$_6$)alkylsulfonyl with 1-9 identical or different halogen atoms comprising (i) reacting, a compound of formula (IV) or a salt thereof

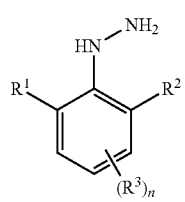

IV in which R$^1$, R$^2$, R$^3$ and n have the above mentioned meanings, with a compound of formula (V) as either E- or Z-isomer

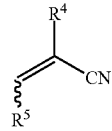

V in which-R$^4$ and R$^5$ have the above mentioned meanings, in the presence of a catalytic amount of base, to obtain a compound of formula (III)

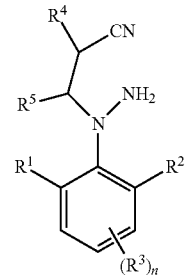

III in which-R$^1$, R$^2$, R$^3$, R$^4$, R$^5$ and n have the above mentioned meanings, and (ii) said compound of formula (III) is, cyclized in the presence of an acid to provide a compound of formula (II)

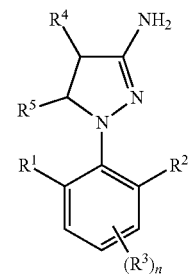

II in which-R$^1$, R$^2$, R$^3$, R$^4$, R$^5$ and n have the above mentioned meanings, and (iii) said compound of formula (II) is, converted in the presence of an oxidant, a catalytic amount of an iodide source and an organic acid, to a compound of formula (I).

2. Process according to claim 1 wherein

R$^1$ represents fluoro

R$^2$ represents fluoro n represents 0,

R$^4$ represents hydrogen and

R$^5$ represents hydrogen.

3. Process according to claim 2 additionally comprising reacting the compound obtained by the process according to claim 2 with a compound of formula (VI)

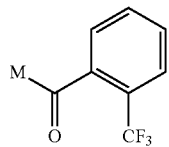
(VI)

wherein
M represents halogen, hydroxy, alkoxy, alkylsulphanyl, acyloxy, N-heterocyclyl or represents hydroxyl, to obtain the compound of formula (VII)

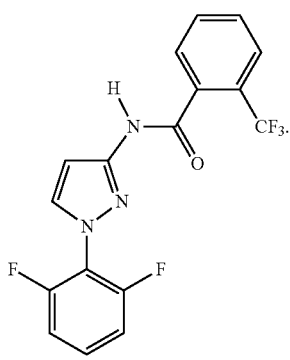
(VII)

4. Process according to claim 1, comprising (ii) and (iii).
5. Process according to claim 4, comprising (iii).
6. The compound of formula

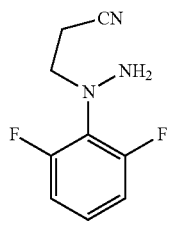 [SMILES: N#CCCN(N)c1c(F)cccc1F]

and/or a salt thereof.

7. Process for preparation of the compound according to claim 6 wherein the compound of formula

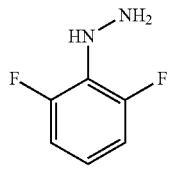

or a salt thereof is reacted with acrylonitrile of formula

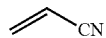

in the presence of a catalytic amount of base.

8. Process according to claim 1, wherein
$R^1$, $R^2$ and $R^3$ represent independently of one another bromo, chloro, fluoro, cyano, $(C_1$-$C_3)$alkyl, $(C_1$-$C_3)$alkoxy, trifluoromethyl, trifluoromethoxy, $(C_1$-$C_3)$alkylthio, n represents a number from the group consisting of 0 and 1, where for n=1 $R^3$ is preferred in position 4 and $R^4$ and $R^5$ represent independently of one another hydrogen, cyano, $(C_1$-$C_3)$alkyl, $(C_1$-$C_3)$alkoxy, trifluoromethyl, $(C_1$-$C_3)$alkylthio.

9. Process according to claim 1, wherein
$R^1$, $R^2$ and $R^3$ represent independently of one another chloro, fluoro, tifluoromethyl, n represents a number from the group consisting of 0 and 1, where for n=1 $R^3$ is in position 4 and $R^4$ and $R^5$ represent hydrogen.

10. Process according to claim 1, wherein
$R^1$, $R^2$ and $R^3$ represent independently of one another halogen, cyano, nitro, $(C_1$-$C_3)$alkyl, $(C_2$-$C_3)$alkenyl, $(C_2$-$C_3)$alkynyl, $(C_3$-$C_6)$cycloalkyl, $(C_1$-$C_3)$alkoxy, phenyl$(C_1$-$C_3)$alkyl, aryl, cyano$(C_1$-$C_3)$alkyl, halogen$(C_1$-$C_3)$alkyl with 1-7 identical or different halogen atoms, halogen$(C_1$-$C_3)$alkoxy with 1-7 identical or different halogen atoms, $(C_1$-$C_3)$alkoxycarbonyl$(C_1$-$C_3)$alkyl, $(C_1$-$C_3)$alkoxy$(C_1$-$C_3)$alkyl, $(C_1$-$C_3)$alkylthio, halogen$(C_1$-$C_3)$alkylthio with 1-7 identical or different halogen atoms, $(C_1$-$C_3)$alkylsulfinyl, $(C_1$-$C_3)$alkylsulfonyl, n represents a number from the group consisting of 0, 1 and 2, where for n>1, $R^3$ may be identical or different and $R^4$ and $R^5$ represent independently of one another hydrogen, cyano, $(C_1$-$C_3)$alkyl, $(C_3$-$C_6)$cycloalkyl, $(C_1$-$C_3)$alkoxy, phenyl$(C_1$-$C_3)$alkyl, aryl, heteroaryl, cyano$(C_1$-$C_3)$alkyl, halogen$(C_1$-$C_3)$alkyl with 1-7 identical or different halogen atoms, halogen$(C_1$-$C_3)$alkoxy with 1-7 identical or different halogen atoms, $(C_1$-$C_3)$alkoxycarbonyl$(C_1$-$C_3)$alkyl, $(C_1$-$C_3)$alkoxy$(C_1$-$C_3)$alkyl, $(C_1$-$C_3)$alkylthio, halogen$(C_1$-$C_3)$alkylthio with 1-9 identical or different halogen atoms.

\* \* \* \* \*